US008620449B2

(12) United States Patent
Zhao et al.

(10) Patent No.: US 8,620,449 B2
(45) Date of Patent: Dec. 31, 2013

(54) IMPLANTABLE MEDICAL DEVICE ANTENNA

(75) Inventors: Yanzhu Zhao, Blaine, MN (US); Quentin S Denzene, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 763 days.

(21) Appl. No.: 12/841,778

(22) Filed: Jul. 22, 2010

(65) Prior Publication Data
US 2012/0001812 A1    Jan. 5, 2012

Related U.S. Application Data

(60) Provisional application No. 61/360,395, filed on Jun. 30, 2010.

(51) Int. Cl.
*A61N 1/00*  (2006.01)
*A61N 1/08*  (2006.01)
*H01Q 1/36*  (2006.01)

(52) U.S. Cl.
USPC ............... 607/70; 607/32; 607/36; 343/895

(58) Field of Classification Search
USPC ................ 607/32, 36, 60; 343/895, 718
See application file for complete search history.

(56) References Cited

U.S. PATENT DOCUMENTS

| | | | |
|---|---|---|---|
| 6,008,762 A | 12/1999 | Nghiem | |
| 6,240,317 B1 | 5/2001 | Villaseca et al. | |
| 6,300,914 B1 | 10/2001 | Yang | |
| 6,708,065 B2 | 3/2004 | Von Arx et al. | |
| 6,809,701 B2 | 10/2004 | Amundson et al. | |
| 7,016,733 B2 | 3/2006 | Dublin et al. | |
| 7,047,076 B1 | 5/2006 | Li et al. | |
| 7,181,505 B2 | 2/2007 | Haller et al. | |
| 7,307,597 B2 * | 12/2007 | Okayama | 343/788 |
| 7,309,262 B2 | 12/2007 | Zart et al. | |
| 7,317,946 B2 * | 1/2008 | Twetan et al. | 607/60 |
| 7,363,087 B2 | 4/2008 | Nghiem et al. | |
| 7,463,930 B2 | 12/2008 | Housworth et al. | |

(Continued)

FOREIGN PATENT DOCUMENTS

| | | |
|---|---|---|
| JP | 2005341091 A | 12/2005 |
| JP | 2007067755 A | 3/2007 |

OTHER PUBLICATIONS

Reply to Written Opinion from corresponding PCT application serial No. PCT/US2011/034363 filed Apr. 27, 2012 (14 pages).

(Continued)

*Primary Examiner* — Hoang V Nguyen
(74) *Attorney, Agent, or Firm* — Stephen W. Bauer; Michael J. Ostrom

(57) ABSTRACT

This disclosure is directed to a three-dimensional antenna that may be used for an implantable medical device (IMD). The antenna includes a first antenna portion that includes a plurality of segments arranged substantially parallel to one another in a first plane. The antenna further includes a second antenna portion that includes a plurality of segments arranged substantially parallel to one another in a second plane that is substantially parallel to the first plane. The antenna further includes a third antenna portion that includes a plurality of segments arranged substantially parallel to one another in a third plane. The plurality of segments of the third portion are coupled between segments of the first and second portions. The third plane is arranged substantially perpendicular to the first plane and the second plane.

25 Claims, 15 Drawing Sheets

(56) References Cited

U.S. PATENT DOCUMENTS

| | | | |
|---|---|---|---|
| 7,467,014 B2 * | 12/2008 | Fuller et al. | 607/60 |
| 7,554,493 B1 * | 6/2009 | Rahman | 343/702 |
| 7,720,544 B2 * | 5/2010 | Christman et al. | 607/60 |
| 8,219,204 B2 * | 7/2012 | Mateychuk | 607/60 |
| 2003/0001794 A1 | 1/2003 | Park et al. | |
| 2004/0150567 A1 * | 8/2004 | Yuanzhu | 343/700 MS |
| 2005/0203583 A1 | 9/2005 | Twetan et al. | |
| 2007/0052594 A1 | 3/2007 | Nevermann | |
| 2007/0100385 A1 | 5/2007 | Rawat et al. | |
| 2007/0240297 A1 | 10/2007 | Yang et al. | |
| 2008/0021522 A1 * | 1/2008 | Verhoef et al. | 607/60 |
| 2008/0039898 A1 | 2/2008 | Lim et al. | |
| 2008/0303728 A1 | 12/2008 | Lee et al. | |
| 2009/0174557 A1 | 7/2009 | Nikitin et al. | |
| 2009/0228074 A1 | 9/2009 | Edgell et al. | |
| 2009/0248112 A1 | 10/2009 | Mumbru et al. | |

OTHER PUBLICATIONS

International Preliminary Report on Patentability from corresponding PCT Application Serial No. PCT/US2011/034363 dated Oct. 26, 2012 (20 pages).

Written Opinion from corresponding PCT Application Serial No. PCT/US2011/034363 dated Jun. 19, 2012 (8 pages).

Reply to Second Written Opinion from corresponding PCT Application Serial No. PCT/US2011/034363 dated Sep. 19, 2012 (16 pages).

International Search Report and Written Opinion of international application No. PCT/US2011/034363, dated Aug. 22, 2011, 14 pp.

\* cited by examiner

IMPLANTABLE MEDICAL DEVICE ANTENNA

This application claims the benefit of U.S. Provisional Application No. 61/360,395, entitled "IMPLANTABLE MEDICAL DEVICE ANTENNA," and filed on Jun. 30, 2010, the entire content of which is incorporated herein by reference.

TECHNICAL FIELD

This disclosure is generally directed to implantable medical devices (IMDs) and, more specifically, this disclosure is directed to antennas for use with an IMD.

BACKGROUND

Implantable medical devices (IMDs) may be configured to provide one or more therapies to a patient and/or sense various physiological signals. For example, an IMD may be implantable within the body of a patient to deliver electrical stimulation therapy such as cardiac stimulation therapy or neurostimulation therapy. Examples of cardiac stimulation therapy include pacing, cardiovoersion or defibrillation therapy. Examples of neurostimulation therapy include spinal cord stimulation, deep brain stimulation, gastric stimulation, peripheral nerve stimulation, or pelvic floor stimulation. In other examples, an IMD may also or instead be configured to delivery drug therapy to a patient.

Due to a need to implant an IMD within the confines of one or more structures of a patient's body, it is typically desirable to design the IMD to be as small as possible and/or to conform to a desired form factor. Due to these requirements, it is often desirable to design components of an IMD to be as small as possible.

SUMMARY

This disclosure is directed to techniques that provide for a three-dimensional antenna that may be used in an implantable medical device. In some aspects, the antenna may be described as a meandering, or serpentine, in that it includes segments that meander in three-dimensions. The antenna described herein may provide beneficial performance characteristics in comparison to other larger antennas. The antenna described herein may further be easy to manufacture, and may be made conformal to a structure in which the antenna is disposed.

In one example, a device is described herein. The device includes a telemetry module. The device further includes an antenna coupled to the telemetry module. The antenna includes a first antenna portion comprising a plurality of segments arranged substantially parallel to one another in a first plane. The antenna further includes a second antenna portion comprising a plurality of segments arranged substantially parallel to one another in a second plane. The antenna further includes a third antenna portion comprising a plurality of segments arranged substantially parallel to one another in a third plane. The plurality of segments of the third portion are coupled between segments of the first and second portions. The third plane is arranged substantially perpendicular to the first plane and the second plane.

In another example, an antenna is described herein. The antenna includes a first antenna portion comprising a plurality of segments arranged substantially parallel to one another in a first plane. The antenna further includes a second antenna portion comprising a plurality of segments arranged substantially parallel to one another in a second plane. The antenna further includes a third antenna portion comprising a plurality of segments arranged substantially parallel to one another in a third plane. The plurality of segments of the third portion are coupled between segments of the first and second portions. The third plane is arranged substantially perpendicular to the first plane and the second plane.

In another example, a method of forming a three-dimensional antenna is described herein. The method includes forming, from a substrate, a one-dimensional serpentine structure that comprises a plurality of segments arranged substantially parallel to one another in a plane. The method further includes forming, from the one-dimensional serpentine structure, a three-dimensional antenna that includes a first portion that includes a plurality of segments arranged substantially parallel to one another in a first plane, a second portion that includes a plurality of segments arranged substantially parallel to one another in a second plane, and a third portion that includes a plurality of segments arranged substantially parallel to one another in a third plane. The plurality of segments of the third portion are coupled between segments of the first and second portions. The third plane is arranged substantially perpendicular to the first plane and the second plane.

The details of one or more examples of the disclosure are set forth in the accompanying drawings and the description below. Other features, objects, and advantages will be apparent from the description and drawings, and from the claims.

DETAILED DESCRIPTION

Figure 1:
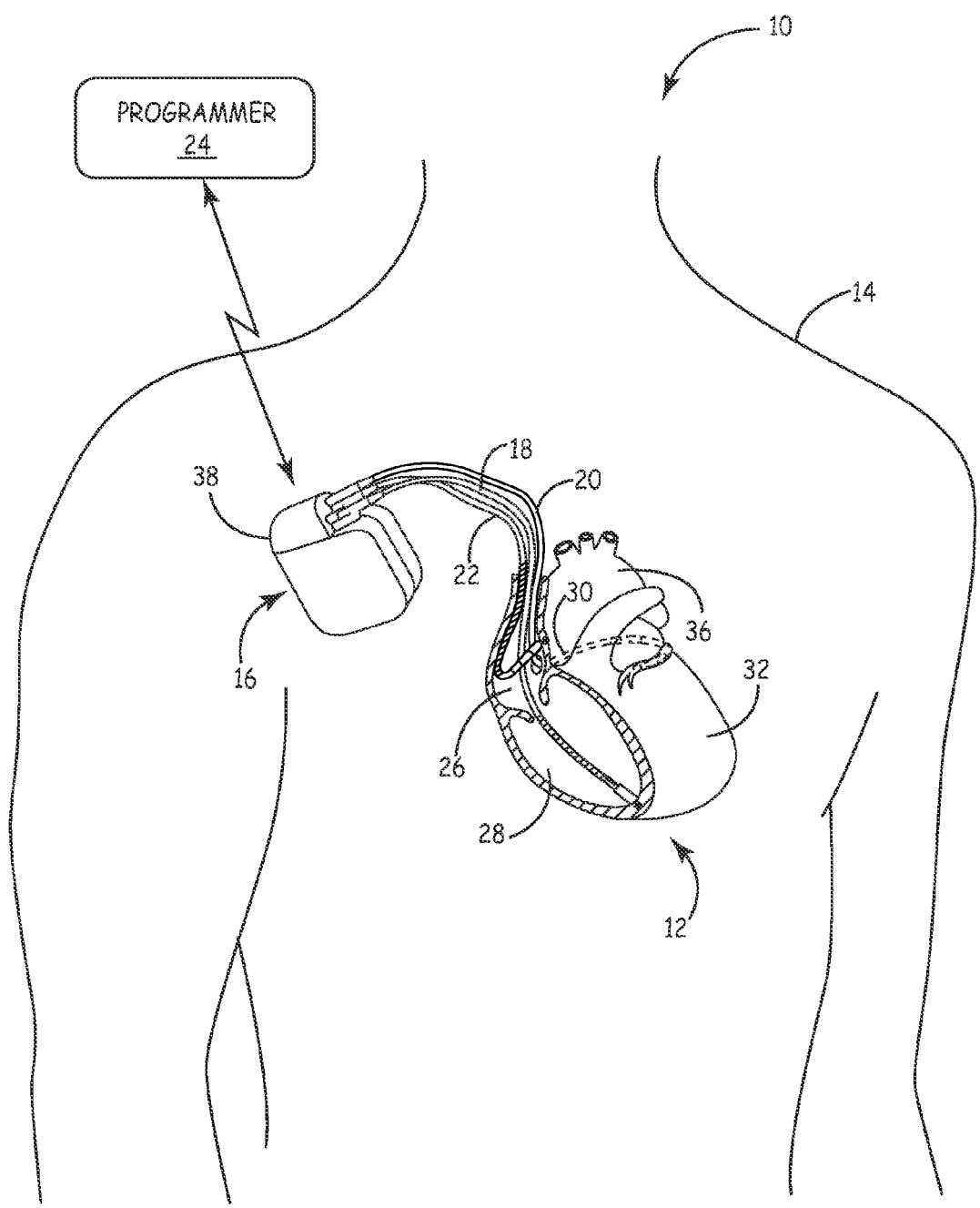
FIG. 1 is a conceptual diagram illustrating one example of an implantable medical device (IMD) implanted within a body of a patient consistent with this disclosure.

FIG. 1 is a conceptual diagram illustrating an example system 10 that may be used for sensing of physiological parameters of patient 14 and/or to provide therapy to heart 12 of patient 14. System 10 depicted in FIG. 1 is provided as only one example of a system that may be utilized according to the disclosure described herein. The techniques of this disclosure may be utilized with systems configured to provide therapy for non-cardiac structures or systems of a patient, including systems that include one or more drug delivery devices and/or systems that include one or more neurological stimulators configured to deliver therapeutic electrical stimulation to one or more neurological structures of a patient. The techniques of this disclosure may further be utilized for systems that include any combination of implantable medical devices, external medical devices, implantable or external leads and/or electrodes, programmers, physicians, or other users.

Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In addition to providing electrical signals to heart 12, IMD 16 may additionally or alternatively provide therapy in the form of electrical signals to other portions of the body, e.g. neurological therapy that provides electrical stimulation to and/or monitors conditions associated with the brain, spinal cord, or other neural tissue of patient 14. IMD 16 may also or instead be adapted to deliver drugs internally or externally of a patient to provide one or more drug based therapies. Further, therapy system 10 may include a single medical device 16, or multiple implantable or external medical devices for specific purposes, e.g. a first medical device to deliver electrical therapy, a second medical device to deliver drug therapy, and/or a third medical device to deliver neurological therapy. Therapy system 10 may further include one or more additional medical devices adapted for sensing various hemodynamic, autonomic, or other conditions, e.g. blood sensors, temperature sensors, patient activity sensors, patient posture sensors, force sensors, blood flow sensors or any other sensor adapted to sense one or more hemodynamic, autonomic, or other indications internal or external to a patient 14.

FIG. 1 depicts one specific example of a therapy system 10 for exemplary purposes. Other configurations are also contemplated and consistent with the disclosure described herein. In the example of FIG. 1, leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation. Additionally, in some examples, an IMD need not be coupled to leads, and instead itself includes a plurality of electrodes, which may be formed on or integrally with a housing of the IMD. An example of such an IMD is the Reveal® monitor, which is commercially available from Medtronic, Inc. of Minneapolis, Minn.

IMD 16 may sense electrical signals attendant to the depolarization and repolarization of heart 12 via electrodes (not shown in FIG. 1) coupled to at least one of the leads 18, 20, 22. Electrodes may also be disposed at one or more locations at a housing of IMD 16. Electrodes may also be external to a patient, and also may included in one or more additional IMDs, e.g. a dedicated sensor IMD.

System 10 may include system programmer 24. Programmer 24 may comprise a handheld computing device, computer workstation, or networked computing device. Programmer 24 may include a user interface that receives input from a user, e.g. physician or other caregiver. It should be noted that the user may also interact with programmer 24 remotely via a networked computing device. In some examples, such as in the case of drug delivery devices or neurostimulators, an additional programmer may be provided for use by patient 14. Also, in some examples, additional devices such as monitoring devices may be provided for retrieving or receiving information from IMD 16.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16 to initiate or titrate (adjust) therapy provided by the IMD 16. The term titrate as utilized herein is intended to encompass any adjustment to a therapy provided by a medical device, e.g. IMD 16, including adjustment of parameters of cardiac or neurological electrical stimulation therapy, drug therapy, or the like.

For example, the user may use programmer 24 to retrieve information from IMD 16 regarding heart 12 activity (e.g., a patient's heart rate), including trends therein over time. As another example, the user may use programmer 24 to retrieve information from IMD 16 regarding other sensed physiological parameters of patient 14, such as intracardiac or intravascular pressure, activity, posture, respiration, or thoracic impedance. In some examples, this information may be presented to the user as an alert. For example, heart rate related condition identified based on a detected heart rate signal may trigger IMD 16 to transmit an alert to the user via programmer 24.

IMD 16 and programmer 24 may communicate via wireless communication using any techniques known in the art. Examples of communication techniques may include, for example, low frequency or radio frequency (RF) telemetry, but other techniques are also contemplated. In some examples, programmer 24 may optionally include a programming head that may be placed proximate to the patient's body near the IMD 16 implant site in order to improve the quality or security of communication between IMD 16 and programmer 24. In other examples, programmer 24 and IMD 16 may communicate without the use of a programming head. Wireless telemetry may be conducted using a transmitter/receiver in IMD 16 and a transmitter/receiver in programmer 24. The transmitters and receivers may operate in any of a variety of different wireless telemetry bands such as the Medical Implant Communication Services (MICS) band at 402-405 MHz, the Medical External Data Service (MEDS) band at 401-402 MHz and 405-406 MHz or the frequency ranges of the Industrial, Scientific and Medical (ISM) band.

Although not depicted in FIG. 1, IMD 16 may include one or more antennas to facilitate IMD 16 communications, e.g., communications with programmer 24 or other devices. An antenna of IMD 16 may be coupled to electrical circuitry of IMD 16, which forms a transmitter and/or receiver, to transmit or receive information to and from one or more other devices such as other devices also implanted within patient 14, or other devices external to patient 14 (e.g., programmer 24). An IMD 16 antenna may be configured to improve an ability of IMD 16 to receive and/or transmit signals, for example radio frequency (RF) signals. In some examples, an IMD 16 antenna may be disposed within a header portion 38 of IMD 16. However one or more antennas may also or instead be disposed in other portions of IMD 16.

Figure 2:
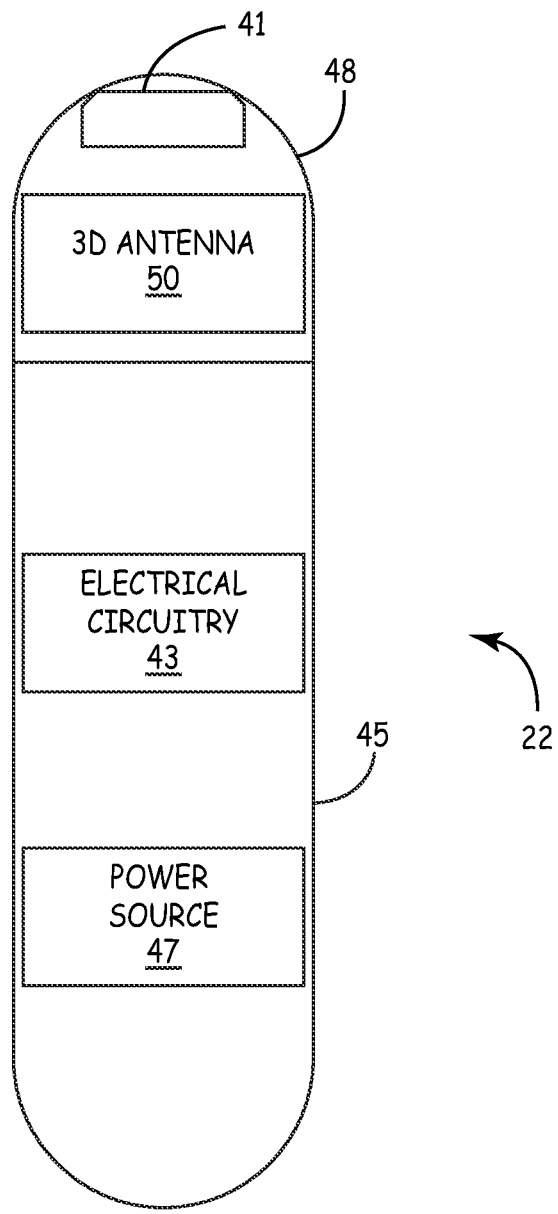
FIG. 2 is a conceptual diagram illustrating one example of an elongated IMD consistent with this disclosure.

FIG. 2 is a conceptual diagram illustrating an alternative example of an IMD 22 that may include a three-dimensional (3D) antenna consistent with the techniques of this disclosure. As shown in FIG. 2, IMD 22 differs from IMD 12 shown in FIG. 1 in that IMD 22 presents an elongated external housing 45. External housing 45 is elongated in the sense that it includes at least one dimension (a height in the example of FIG. 2) that is substantially greater than second and third dimensions (e.g., a width and length) of the external housing 45.

For some applications, an IMD 22 that includes an elongated external housing 45 may be advantageous for a number of reasons. For example, antenna 22 may be sized and shaped to be more easily disposed in smaller regions of a patient's body 14. IMD 22 may be adapted to be disposed in various sub-cutaneous, intravascular (e.g., within a vein our artery of a patient), or other locations within a patient 14.

In some examples, similar to IMD 12 shown in FIG. 1, IMD 22 may include one or more leads (not shown in FIG. 2) that extend into the heart 12 of patient 14 to sense electrical activity of heart 12 and/or deliver electrical stimulation to heart 12. In other examples, IMD 22 itself may instead include one or more electrodes (e.g., electrode 41) for delivery of electrical stimulation and/or to sense electrical or other indications of a patient's health status. In still other examples, IMD 22 may not be configured to delivery any therapy e.g., electrical stimulation, to a patient. According to these examples, IMD 22 may merely include, at or near a housing 45 of IMD, one or more sense electrodes (e.g., electrode 41 depicted in FIG. 2) and/or one or more other sensing elements to detect patient conditions. IMD 22 may be configured to communicate with one or more other IMDs implanted within a patient via antenna 50, e.g., IMD 12 depicted in FIG. 1, for example, to communicate signals indicative of measured indications of a patient's health status. IMD 22 may further or instead be configured to communicate with one or more external devices, such as programmer 24 depicted in FIG. 1.

As shown in FIG. 2, IMD 22 may include a header portion 48. Header portion 48 may be configured to house an antenna 50 and/or other components of IMD 22. For example, header 48 may be configured to house one or more electrodes 41 of IMD 22. As also shown in FIG. 2, IMD 22 may include one or more electrical circuitry 43 comprising one or more electrical circuits configured to perform functionality of IMD 22. For example, the electrical circuitry 43 may be coupled to antenna 50 to receive and/or transmit signals. The one or more electrical circuits may further operate IMD 22 to detect patient conditions. As also shown in FIG. 2, IMD 22 includes at least one power source 47. The at least one power source 47 may provide energy to power components of IMD 22, such as electrical circuitry 43 of IMD 22. In one example, power source 47 may be a battery or other charge storage device. In other examples, power source 47 may be a fuel cell or other similar device configured to generate power for IMD 22, for example, a fuel cell configured to convert glucose or other substances commonly found within the human body to power IMD 16.

FIGS. 1 and 2 depict two respective examples of IMDs 12 and 22 that may be implanted in a patient. A three-dimensional antenna 50 as described herein may be utilized in devices similar to those depicted in FIGS. 1 and 2, and in other types of IMDs having any of a number of different shapes. Additionally, antenna 50 may be utilized in other devices, components or modules that are not configured for implantation. For example, antenna 50 may be used in a communication module, such as the communication module described in commonly assigned U.S. Pat. No. 7,181,505, entitled "SYSTEM AND METHOD FOR REMOTE PROGRAMMING OF AN IMPLANTABLE MEDICAL DEVICE" or the programmer module described in commonly assigned U.S. Pat. No. 7,463,930, entitled "IMPLANTABLE MEDICAL DEVICE PROGRAMMER MODULE FOR USE WITH EXISTING CLINICAL INSTRUMENTATION." Also, antenna 50 may be used in any device for communication purposes, whether the device is used for medical applications or not, such as a cellular telephone, smart phone, personal digital assistant (PDA), pager, a body-worn communication device (e.g., watch) or other electronic device.

Figure 2A:
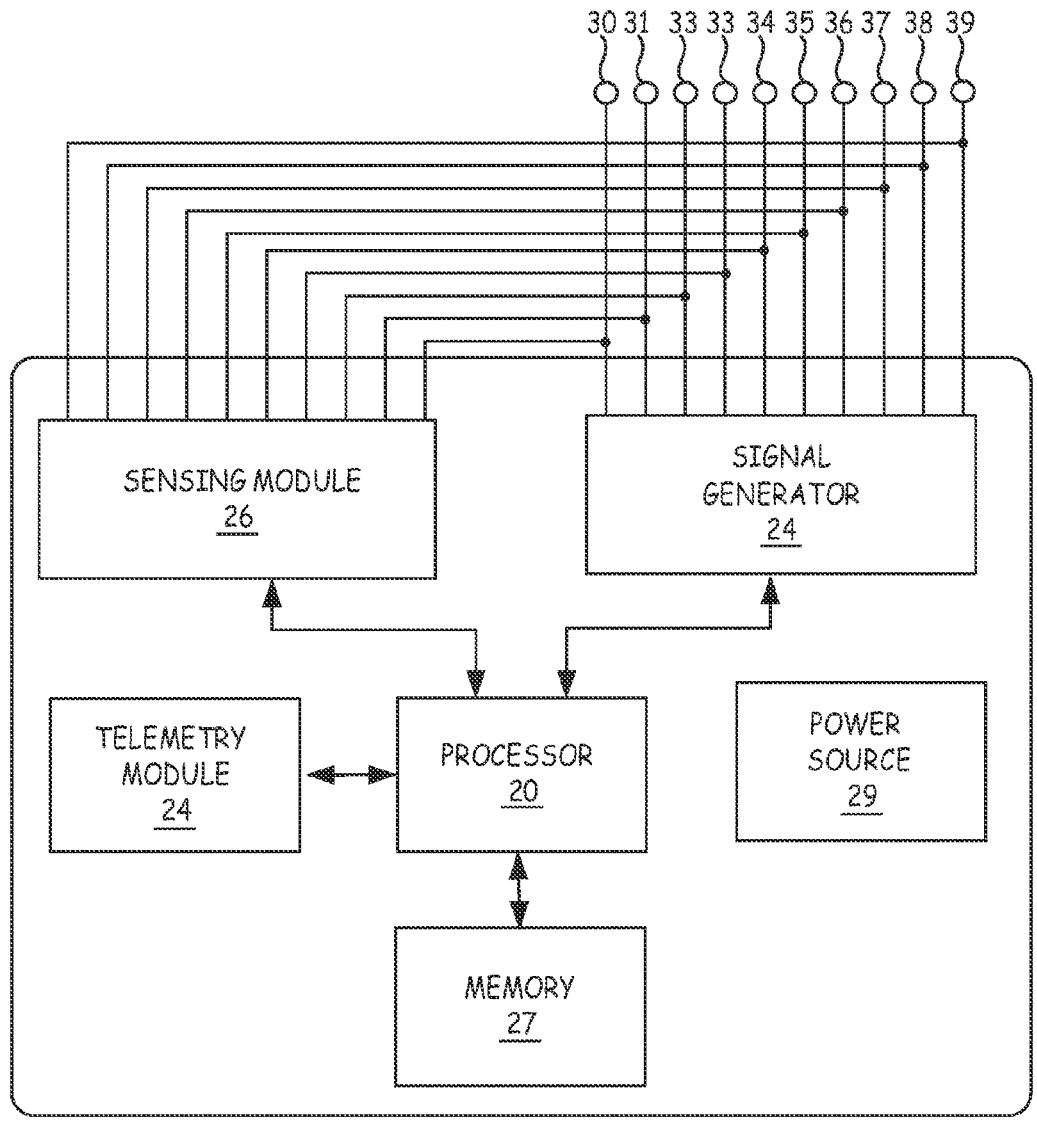
FIG. 2A is a block diagram illustrating one example an arrangement of an IMD that may include an antenna consistent with this disclosure.

FIG. 2A is a block diagram that illustrates an example configuration of an IMD (e.g., IMDS 12 and 22 depicted in FIGS. 1 and 2) that may include an antenna consistent with this disclosure. In the illustrated example, the IMD includes a processor 20, memory 27, signal generator 24, sensing module 26, telemetry module 28, and power source 29. Memory 27 includes computer-readable instructions that, when executed by processor 20, cause the IMD and processor 20 to perform various functions attributed to the IMD and processor 20 herein. Memory 27 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 20 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 20 herein may be embodied as software, firmware, hardware or any combination thereof.

Processor 20 may control signal generator 24 to deliver stimulation therapy to heart 12 according to a selected one or more therapy programs, which may be stored in memory 27. For example, processor 20 may control stimulation generator 24 to deliver electrical pulses with the amplitudes, pulse widths, frequency, or electrode polarities specified by the selected one or more therapy programs.

Signal generator 24 is electrically coupled to electrodes 30-39, e.g., via conductors of a respective lead or housing electrode. In the illustrated example, signal generator 24 is configured to generate and deliver electrical stimulation therapy to heart 12. For example, signal generator 24 may deliver defibrillation shocks to heart 12 via at least two electrodes. Signal generator 24 may deliver pacing pulses via ring electrodes coupled to leads, and/or helical electrodes of leads. In some examples, signal generator 24 delivers pacing, cardioversion, or defibrillation stimulation in the form of electrical pulses.

Electrical sensing module 26 monitors signals from at least one of electrodes 30-39 in order to monitor electrical activity of heart 12. Processor 20 may control the functionality of sensing module 26 by providing signals to one or more of electrodes 30-39.

Sensing module 26 may include one or more detection channels, each of which may comprise an amplifier. The detection channels may be used to sense cardiac signals. Some detection channels may detect events, such as R- or P-waves, and provide indications of the occurrences of such events to processor 20. One or more other detection channels may provide the signals to an analog-to-digital converter, for processing or analysis by processor 20. In response to the signals from processor 20, sensing module 26 may couple selected electrodes to selected detection channels.

Although not illustrated in FIG. 2A, an IMD 12, 22 as described herein may include or be coupled to any of a variety of other sensors that provide a signal that varies as a function of a physiological parameter of the patient. In some examples, the signals vary as a function of the mechanical contraction of heart 12. Examples of sensors that provide signals that vary as a function of the mechanical contraction of the heart include pressure sensors, such as capacitive pressure sensors, accelerometers, and piezoelectric elements. Such sensors may be located on one or more leads, located at or near an housing of IMD 12, 22, or may be part of a separate device implanted on or in the heart, or otherwise implanted within patient 14. Likewise, the IMD may include other therapy modules in addition to or instead of signal generator 24. For example, the IMD may include a pump and reservoir that is controlled by processor 20 to deliver a drug or other therapeutic agent to patient 14.

FIGS. 3-6 illustrate generally various perspective views of an example 3D antenna 50 consistent with this disclosure. As shown in FIGS. 3-6, antenna 50 may include a first portion 52, a second portion 54, and a third portion 56. First portion 52 of antenna 50 includes a plurality of segments 62A-62E. The plurality of segments 62A-62E are arranged substantially parallel to one another in a plane.

First portion 52 of antenna 50 further includes one or more connector segments 63A-63C arranged perpendicular to the plurality of segments 62A-62E and in the same plane as the plurality of segments 62A-62E. One or more of connector segments 63A-63C may be formed integral to one or more of the plurality of segments 62A-62E. Connector segments 63A-63C may couple one or more of the plurality of segments 62A-62E to one another. For example, connector portion 63A is arranged substantially perpendicular and integral to segments 62A and 62B. Connector portion 63A couples segments 62A and 62B to one another in the plane of the first portion 52.

As also shown in FIGS. 3-6, second portion 54 of antenna 50 also comprises a plurality of segments 64A-64E arranged substantially parallel to one another in a second plane different than the plane (first plane) of the first portion 52. As also shown in FIGS. 3-6, second portion 54 of antenna 50 further includes one or more connector segments 65A-65C arranged perpendicular to the plurality of segments 64A-64E and in the same plane (the second plane) as the plurality of segments 64A-64E. As shown in the example of FIGS. 3-6, connector segments 65A-65C may be formed integral to one or more of the plurality of segments 64A-64E. Connector segments 65A-65C may couple one or more of the plurality of segments 64A-64E to one another. For example, connector portion 65B is arranged substantially perpendicular (and integral to) segments 64B and 64C. Connector portion 65B couples segments 64B and 64C to one another in the plane of the second portion 54 (second plane).

As also shown in FIGS. 3-6, third portion 56 of antenna 50 also comprises a plurality of segments 66A-66E arranged substantially parallel to one another in a third plane different than the first and second planes of the first and second portions 52, 54, respectively. The third plane may be substantially perpendicular to the first and second planes. Also, third portion 56 does not include any segments perpendicular to the third plane. Thus, third portion 56 does not include any connector segments, such as connector segments 63A-63C and 65A-65C of first portion 52 and second portion 54, respectively, of antenna 50. Also, segments 66A-66E may have a length that is substantially shorter than a corresponding length of segments 62A-62E and/or segments 64A-64E. For example, as shown in FIGS. 3-6, a length of segment 62D traversing the first plane is substantially greater than a corresponding length of segment 66E traversing the third plane.

As shown in FIGS. 3-6, at least some of the segments 66A-66E of the third portion 56 are coupled between segments of the first and second portions 52, 54. In some examples, at least some of the segments 66A-66E of the third portion 56 are formed integral to (formed of the same piece) one or more of the plurality of segments 62A-62E, 64A-64E of the first and second portions, respectively. In other examples not depicted in FIGS. 3-6, at least some of the segments 66A-66E may be formed of different pieces of material according to the arrangement of FIGS. 3-6. In one example, one or more of segments 66A-66E may be substantially perpendicular to one or more of segments 62A-62E, 64A-64E. In this manner, a junction between one or more of segments 66A-66E and one or more of segments 62A-62E, 64A-64E may form about a 90 degree angle.

As also shown in FIGS. 3-6, third portion 56 of antenna 50 is arranged in a third plane that is substantially perpendicular to the first and second planes in which the first and second portions 52 and 54 are respectively arranged. Third portion 56 may therefore be considered to form an angle of about 90 degrees with respect to the first and second portions 52, 54.

The various segments 62A-62E, 63A-63C, 64A-64E, 65A-65C, and 66A-66E of antenna 50 may be formed from one or more materials that have properties desirable to function as an antenna for communications. For example, the various segments of antenna 50 may be formed of a metallic material. Examples of materials that may be used to form the various segments of antenna 50 include aluminum, niobium, titanium, gold, and platinum, or their alloys. In some examples, the various segments of antenna 50 may be formed of a metallic coating on one or more substrate materials (e.g., a dielectric material). In some examples, the various segments of antenna 50 may be formed of one or more biocompatible materials. In one example, it may be desirable for the various segments 62A-62E, 63A-63C, 64A-64E, 65A-65C, and 66A-66E of antenna 50 to have a radius of about 0.127-0.254 millimeters, however other radii are also contemplated.

According to the example antenna 50 shown in FIGS. 3-6, segments 62A-62E and 64A-64E are depicted as substantially straight, or not including any arcuate, or curved, sections. According to other examples not depicted in FIGS. 3-6, segments 62A-62E and 64A-64E may instead include at least one substantially arcuate section, or a junction between any of the plurality of segments of antenna 50 may also be curved or rounded.

In one example, one or more of segments 62A-62E and 64A-64E may bow outwards or inwards with respect to the first and second planes in which segments 62A-62E and 64A-64E are respectively arranged. According to these examples, a junction between one or more of segments 66A-66E and one or more of segments 62A-62E, 64A-64E may not form an angle of exactly 90 degrees. Instead, one or more of segments 66A-66E may be considered substantially perpendicular to one or more of segments 62A-62E, 64A-64E in that a junction between the segments forms an angle of greater than or less than 90 degrees (e.g., 80-100 degrees).

According to these examples, one or more of segments 66A-66E may be considered to be arranged substantially perpendicular to one or more of segments 62A-62E, 64A-64E. Similarly, according to examples in which one or more of segments 62A-62E, 64A-64E include at least one arcuate section, third portion 56 may be considered arranged in a third plane that is substantially perpendicular to the first and second portions 52, 54, although an angle of greater or less than 90 degrees (e.g., approximately 80-100 degrees) may be formed between the third portion 56 and either of the first and second portions 52, 54.

Above, antenna 50 is described in terms of segments of portions 52, 54, and 56. In other examples, antenna 50 may be described in terms of one or more of segments 62A-62E, 63A-63C, 64A-64E, 65A-65C, and 66A-66E themselves. For example, antenna 50 comprises a first segment 65B. The antenna further includes a second segment 64C coupled to the first segment 65B and arranged substantially perpendicular to the first segment 65B. The antenna further includes a third segment 66C coupled to the second segment 64C and arranged substantially perpendicular to the first 65B and second 64C segments. The antenna further includes a fourth segment 62C coupled to the third segment 66C and arranged substantially perpendicular to the third segment 66C and substantially parallel to the second segment 64C. The antenna further includes a fifth segment 63B coupled to the fourth segment 62C and arranged substantially perpendicular to the fourth segment 62C and substantially parallel to the first segment 65B. In one example, second antenna portion 54 includes the first 62B and second segments 64C, third antenna portion 56 includes the third segment 66C, and second antenna portion 54 includes the fourth 62C and fifth 63B segments.

Antenna 50 may further include a sixth segment 62D coupled to the fifth segment 63B and arranged substantially perpendicular to the fifth segment 63B and substantially parallel to the fourth segment 62C and second segment 64C. According to this example, second antenna portion 54 may includes sixth segment 62D in addition to the fourth 62C and fifth 63B segments. In some examples, any coupling of segments 65B, 64C, 66C, 62C, 63B, and/or 62D may be integral to, or formed of the same piece with, another segment. In some examples, an arrangement of segments as described with respect to segments 65B, 64C, 66C, 62C, 63B, and/or 62D may be repeated as shown in the example of FIGS. 3-6. In other examples, a structure comprising segments 65B, 64C, 66C, 62C, 63B, and/or 62D may be repeated less or more times than the antenna 50 depicted in FIGS. 3-6. In some examples, a number of repetitions of the structure comprising segments arranged such as segments 65B, 64C, 66C, 62C, 63B, and/or 62D are arranged may be selected based on desired characteristics of antenna 50. For example, more or fewer repetitions of the structure comprising segments 65B, 64C, 66C, 62C, 63B, and/or 62D may be selected such that antenna 50 has a desired impedance to match an impedance of electrical circuitry coupled to antenna 50 (e.g., electrical circuitry 43 depicted in FIG. 2) and/or a housing of electrical circuitry coupled to antenna 50 (e.g., housing 45 depicted in FIG. 2).

Figure 3:
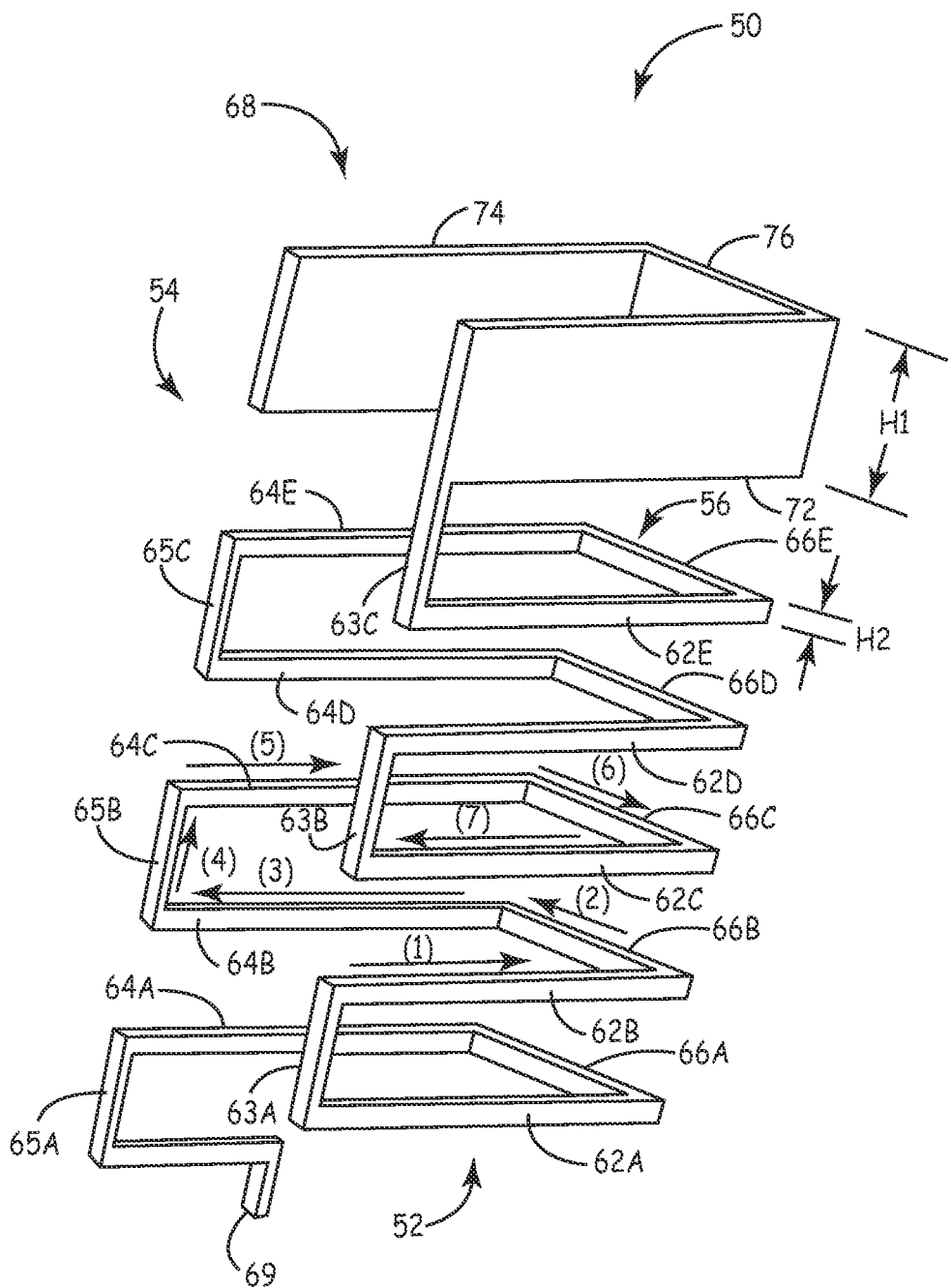
FIGS. 3-6 are a conceptual diagram that illustrate various perspective views of a three-dimensional (3D) antenna consistent with this disclosure.
Figure 4:
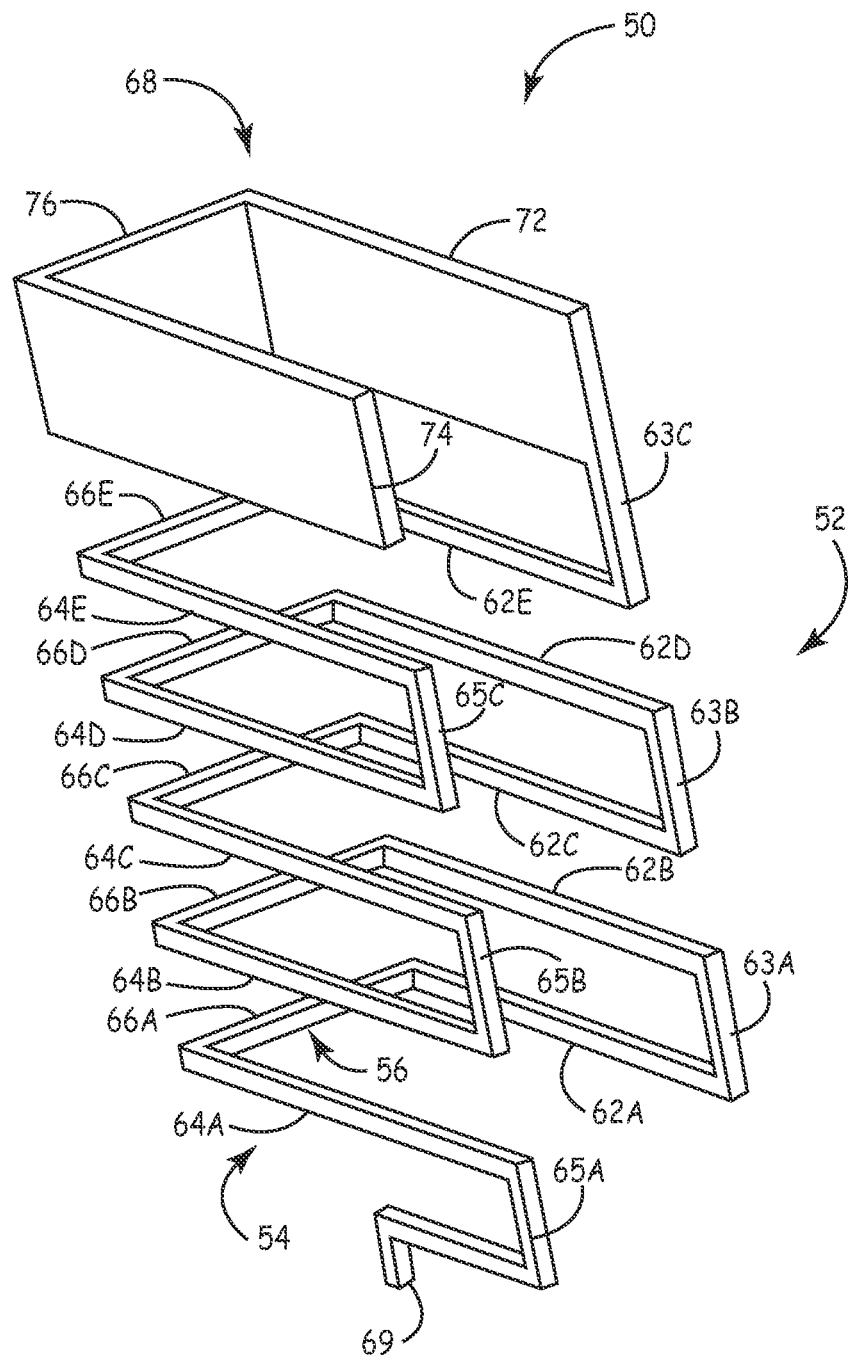
Figure 5:
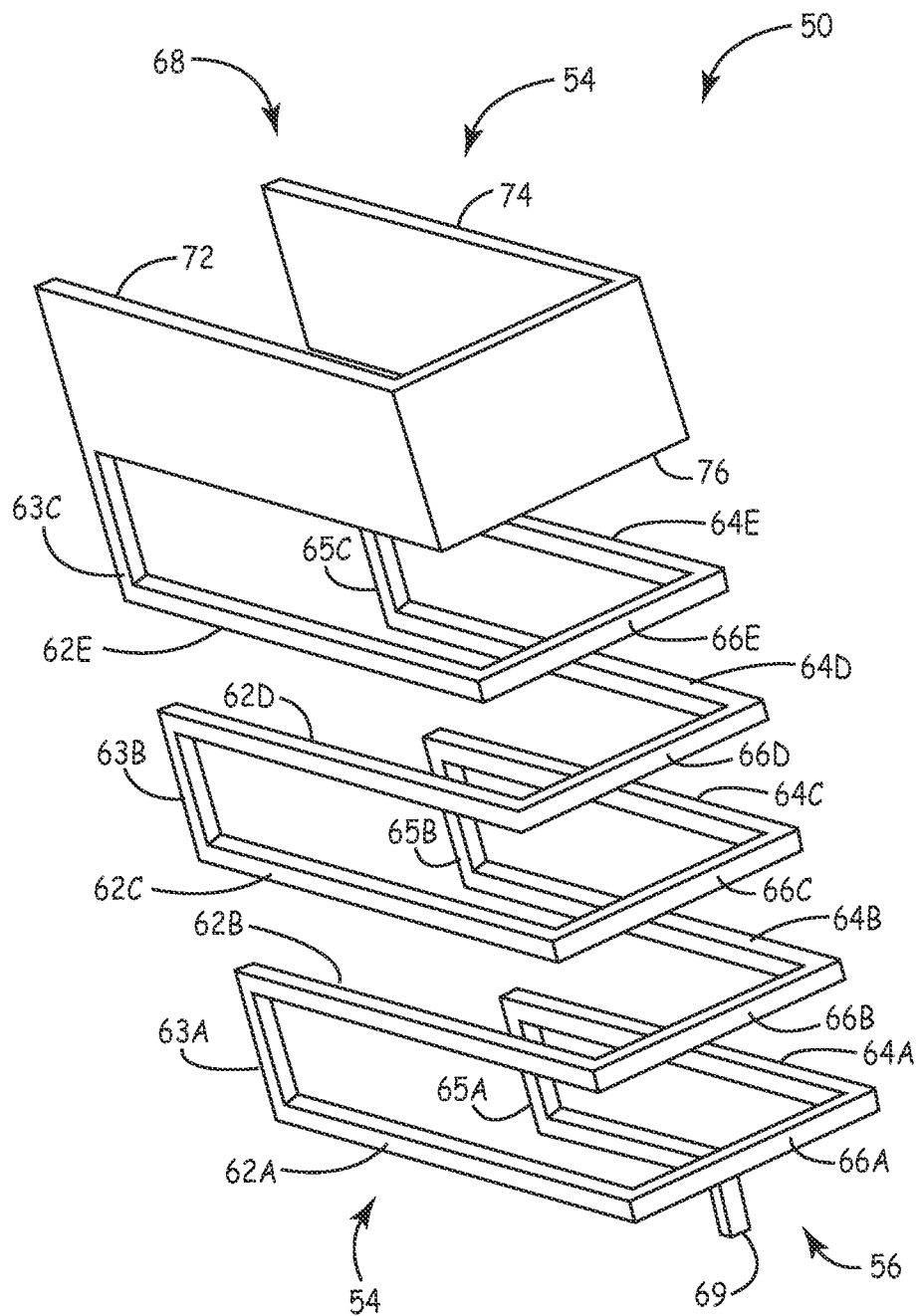
Figure 6:
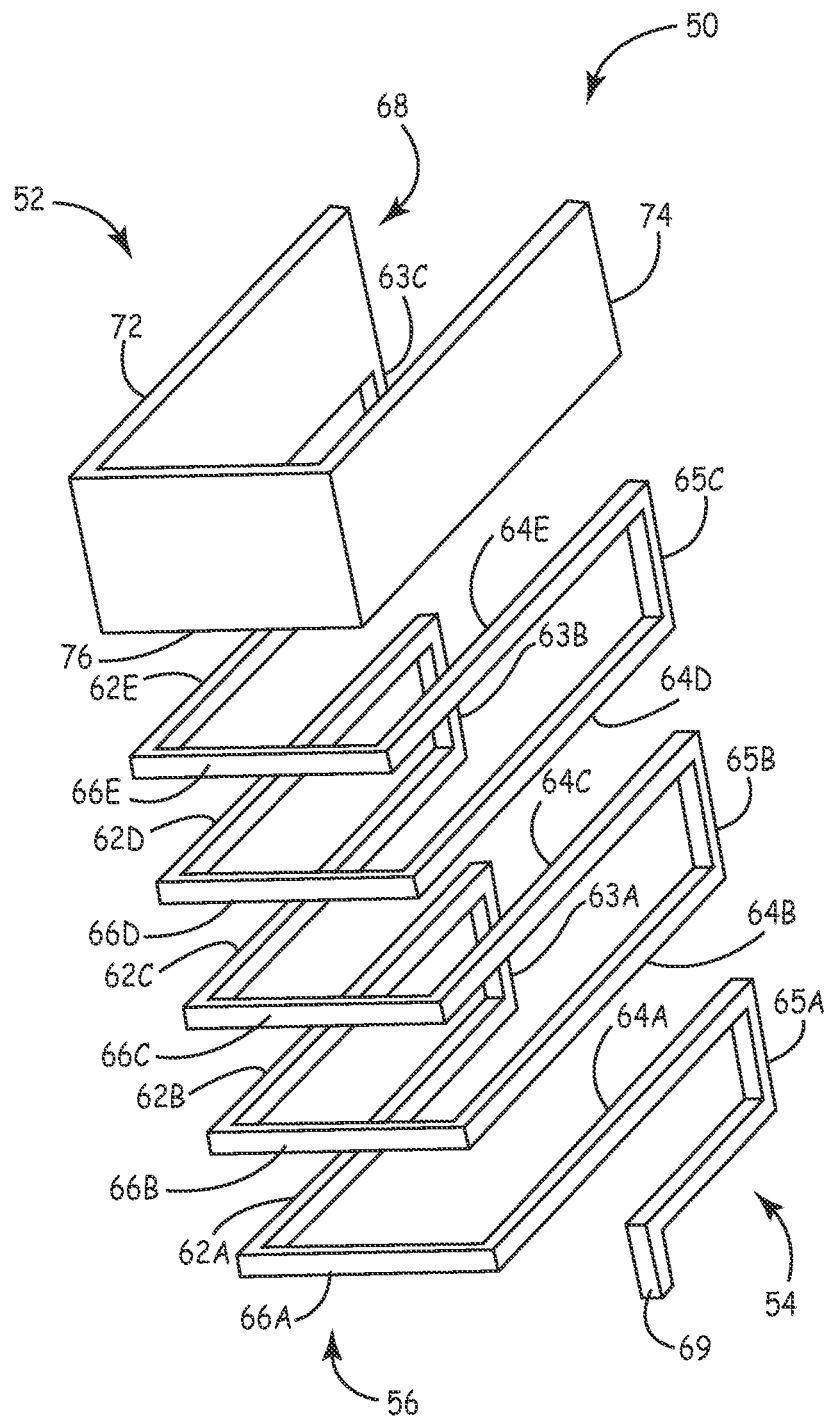

Antenna 50 as depicted in FIGS. 3-6 may be described as an antenna that meanders in three dimensions. Antenna 50 may also be described as comprising a serpentine structure in three dimensions. For example, segment 62A of first portion 52 is arranged in a first plane. Segment 62A is coupled to connector segment 63A, which is also arranged in the first plane. Segment 63A is coupled to segment 62B, which is also arranged in the first plane. Segment 62B is coupled to segment 66B of third portion 56, which is arranged in a plane (e.g., the third plane as described above) substantially perpendicular to the first plane. Segment 66B is coupled to segment 64B of second portion 54, which is arranged in a plane substantially perpendicular to a plane of segment 66B (e.g., the third plane as described above), and parallel to a plane of segments 62A, 63A, and 62B. Thus, as depicted in FIGS. 3-6, antenna 50 may be considered to meander in three dimensions (or be considered a three-dimensional serpentine structure), because the individual segments 62A-62E, 64A-64E, and 66A-66E are arranged such that they "meander" between the first, second, and third planes of antenna 50. In that sense, as shown in FIG. 3, antenna 50 may also be described as comprising a structure that traverses a first plane in a first direction (1), traverses a third plane substantially perpendicular to the first plane in the first direction (2), traverses a second plane substantially perpendicular to the third plane and parallel in the first plane in the first direction (3), extends in a second direction in the second plane (4), traverses the second plane in a third direction (5), traverses the third plane in the third direction (6), and traverses the first plane in the third direction (7).

Antenna 50 depicted in FIGS. 3-6 includes three substantially identical meander sections (e.g. one "meander section" may comprise segments 64A, 66A, 62A, 63A, 62B, and 66B, which "meander" the first, second, and third planes). Antenna 50 as depicted in FIGS. 3-6 is just one example of a three-dimensional meandering antenna consistent with this disclosure. In other examples, antenna 50 may instead include only a single meander section, or more than three meander sections. Selection of a number of meandering sections may depend on a number of factors, such as desired antenna performance (including a desired impedance of antenna 50) and/or size, shape, or form factor considerations. In one specific example, where antenna 50 is configured to be arranged in a header portion (e.g., header 48 of IMD 22 depicted in FIG. 2), with a height of 10 mm, the antenna 50 may include three meandering sections as depicted in FIGS. 3-6. In other examples, where a smaller antenna is desired, more meandering portions may be desirable to achieve similar antenna performance.

In one example, a spacing between segments of antenna 50 (e.g., a spacing between segment 62B and segment 62C), may be selected based on a ratio $L/2n$, where $L$ is a maximum length of a volume of the antenna 50, and $n$ is a number of meandering sections of antenna 50.

As shown in the example antenna of FIGS. 3-6, segments 62A-62E and 64A-64E of first 52 and second 54 portions may have a different length than segments 66A-66E of third portion 66. For example, segments 62A-62E and 64A-64E of first 52 and second 54 portions may have a substantially greater length than segments 66A-66E of third portion 66. In some examples, a ratio of one or more lengths of segments 62A-62E, 64A-64E with respect to a corresponding length of one or more of segments 66A-66E may be selected to improve desirable characteristics (e.g., a gain ratio) of antenna 50 for a particular implementation. In some examples, a ratio of the lengths of segments 62A-62E and 64A-64E to the lengths of segments 66A-66E lengths may range from 2:1 to 3:1. Shorter, or greater lengths may instead be selected to conform antenna 50 as desired to a particular implementation.

As shown in FIGS. 3-6, antenna 50 further may further include coupling structure 69 coupled to segment 65A of second portion 54. Coupling structure 69 may facilitate electrical connection of antenna 50 to one or more other components, such as electrical circuitry configured to communicate signals (e.g., electrical circuitry 43 of IMD 22 depicted in FIG. 2). In this manner, coupling structure 69 may be considered part of the antenna feed line. Another portion of the antenna feed line may be located within the housing of the IMD. Coupling structure 69 may, for example, may be coupled to one or more other components (e.g., via one or more wires, traces, or other conductive structures) using various mechanisms known in the relevant art, including for example soldering, conductive adhesive, and the like. In other examples, coupling structure 69 may connect other portions of antenna 50 (e.g., segments other than segment 65A) to the other components of the IMD.

The exemplary antenna 50 depicted in FIGS. 3-6 may further include at least one antenna loading structure 68. Antenna loading structure 68 may be coupled to at least one of the plurality of segments of first 52, second 54, and third 56 portions of antenna 50. Antenna loading structure 68 may be formed with at least one dimension substantially greater than a corresponding dimension of one or more of segments 62A-62E, 64A-64E, and 66A-66E. For example, as shown in FIGS. 3-6, antenna loading structure 68 is formed of three segments 72, 74, and 76 of the first 52, second 54, and third 56 antenna portions described above. Each of the three segments 72, 74, and 76 has a dimension traversing a direction parallel to the first and second planes (e.g., height H1 in the example of FIG. 3) that is substantially greater than a corresponding dimension (e.g., height H2 in the example of FIG. 3) of the segments 62A-62E, 64A-64E, and 66A-66E parallel to the first, second, and third planes, respectively.

Figure 7:
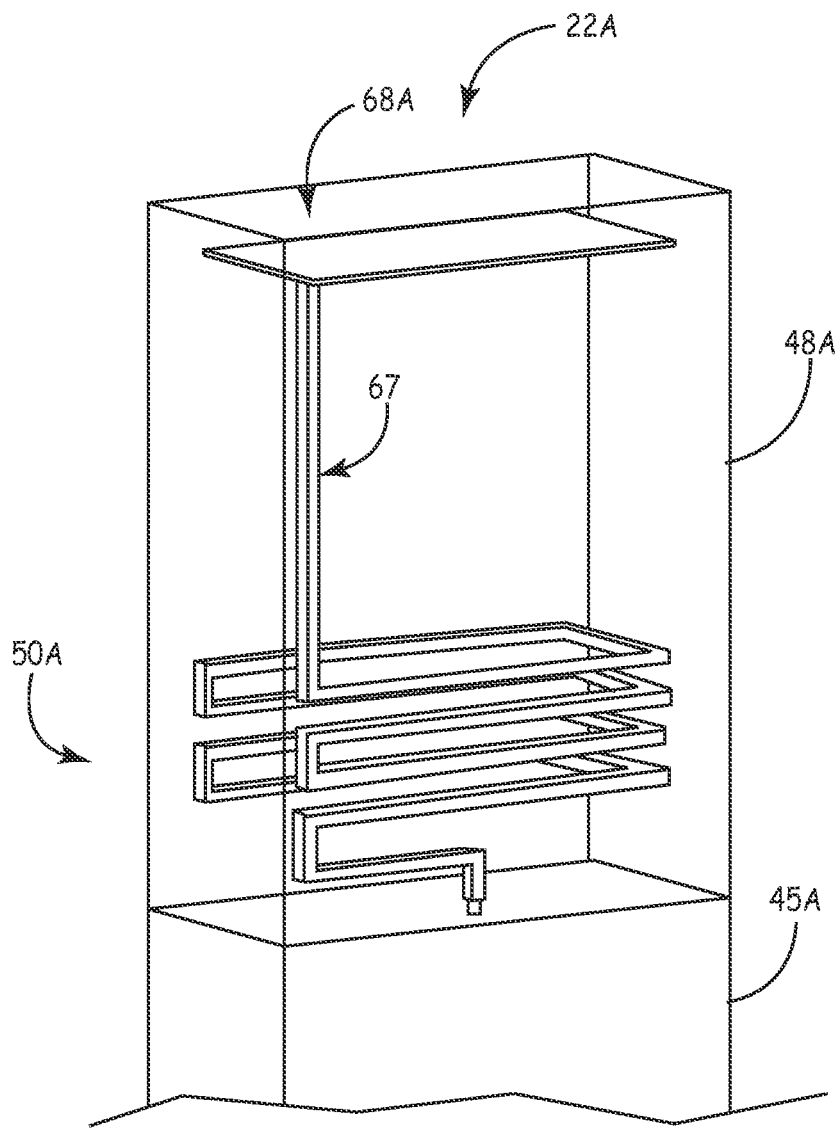
FIG. 7 is a conceptual diagram illustrating one example of a 3D antenna consistent with this disclosure.

In another example as shown in FIG. 7, an antenna loading structure 68A of antenna 50A may comprise a different dimension than that shown in FIGS. 3-6 which is substantially greater than a corresponding dimension of segments 62A-62E, 64A-64E, and 66A-66E. For example, FIG. 7 shows antenna 50A disposed within a header portion 48A of a housing 45A of an implantable medical device 22A. Antenna loading portion 68A of antenna 22A includes a dimension perpendicular to one or more of the first, second, and third planes (e.g., a width of antenna loading portion 68A) described above that is substantially greater than a corresponding dimension (e.g., a width) of segments 62A-62E, 64A-64E, and 66A-66E. As also shown in FIG. 7, antenna loading structure 68A may be arranged more distal from the plurality of segments 62A-62E, 64A-64E, and 66A-66E of antenna 50A. According to these examples, antenna 50A may include at least one additional segment 67 of substantially greater length than a length of the plurality of segments 62A-62E, 64A-64E, and 66A-66E of antenna 50A. The at least one additional segment 67 may serve to couple antenna loading structure 68A to one or more of the plurality of segments 62A-62E, 64A-64E, and 66A-66E.

As discussed above, a spacing between segments of antenna (e.g., a spacing between segments 62B and 62C in the examples of FIGS. 3-6) may be selected according to the ratio L/2n. In one example, a substantially greater dimension of antenna loading portion (e.g., a height in the example of FIG. 3, a width in the example of FIG. 7) may be selected to be substantially equal to a spacing between segments. For example, the substantially greater dimension of antenna loading portion 68 may be substantially equal to L/2n.

Antenna 50 depicted in FIGS. 3-6 shows loading structure 68 and coupling structure 60 coupled to segments 63C and 65A of antenna 50, respectively. In the example of FIGS. 3-6, loading structure 68 and coupling structure 60 are arranged proximal to the plurality of segments (e.g., segments 62A-62E, 64A-64E, and 66A-66E) of antenna 50. In other examples as depicted in FIGS. 8A-8B, one or more of loading structure 68 and coupling structure 69 may be arranged more distal from the plurality of segments of antenna 50. For example, FIG. 8A shows loading structure 68B arranged at greater distance from the plurality of segments 90B, than in the examples of FIGS. 3-6, and coupling structure 69B arranged more proximal to the plurality of segments 90B. FIG. 8B shows loading structure 68C arranged more proximal to the plurality of segments 90C, while coupling structure 69C is arranged more distal from the plurality of segments 90C, relative to the examples of FIGS. 3-6. The example antennas 50B, 50C illustrated in FIGS. 8A and 8B may be advantageous, because they may allow for other components of an IMD to be disposed in an IMD header 48B, 48C along with antenna 50B, 50C, thus allowing for greater flexibility in an arrangement of IMD components.

Figure 9:
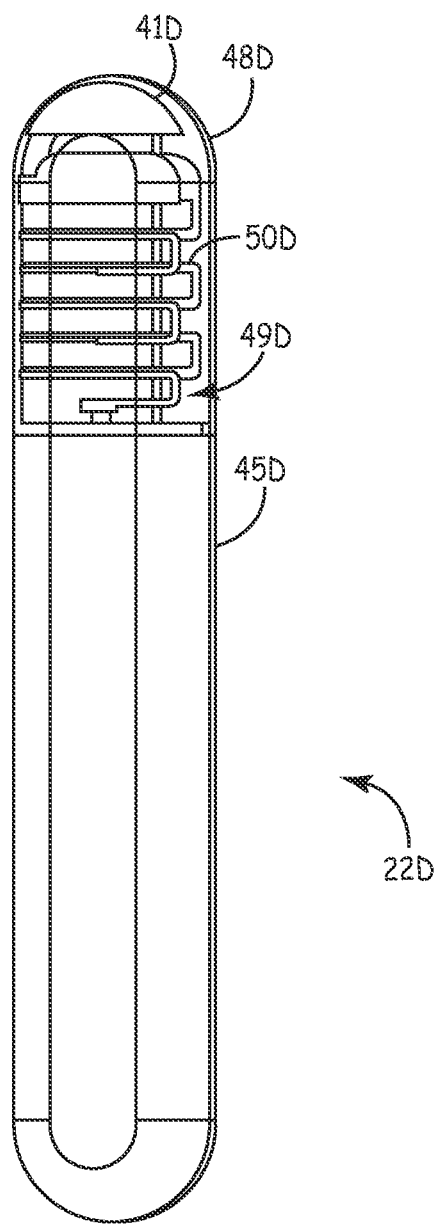
FIGS. 9-10 are conceptual diagrams that illustrate examples of a 3D antenna disposed within a header of an IMD housing consistent with this disclosure.
Figure 10:
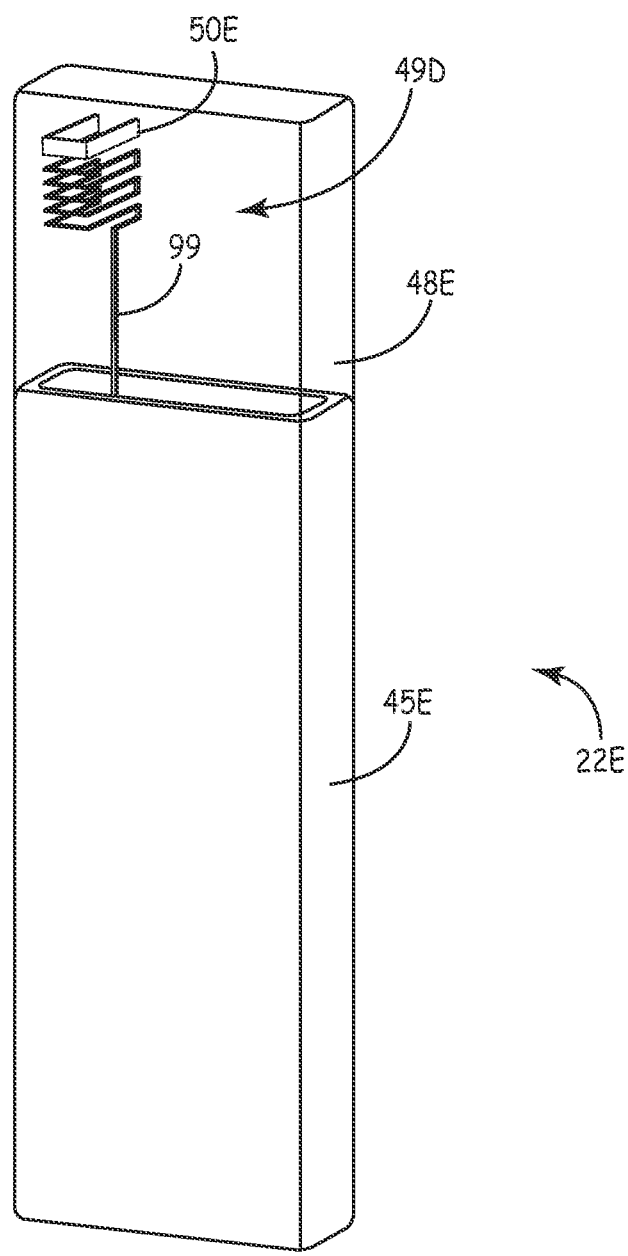

FIGS. 9 and 10 are conceptual diagrams that illustrate examples of IMDs 22D, 22E, that include an antenna 50D, 50E disposed within a header portion 48D, 48E of an IMD housing 45D, 45E consistent with the techniques of this disclosure. IMDS 22D, 22E may be considered to have an elongated housing 45D, 45E, similar to IMD housing 45 depicted in FIG. 2. FIGS. 9 and 10 depict some examples of an antenna 50D, 50E disposed within an IMD housing 45D, 45E. In other examples, an antenna 50D, 50E as described herein may be disposed within a non-header portion of IMD housing 45D, 45E. According to such examples, the housing 45D, 45E may be formed of a non-conductive material. Housing 45D, 45E may include one or more electrical circuits as described above with respect to electrical circuitry 43 of IMD 22 of FIG. 2. The one or more electrical circuits may be coupled to one or more electrodes and/or sensors to provide one or more therapies to a patient and/or sense various physiological signals. For example, the one or more electrical circuits may be coupled to one or more electrodes and/or sensors at or near an exterior surface of housing 45D, 45E. In other examples, the one or more electrical circuits may be coupled to one or more electrodes and/or sensors via or one or more leads coupled to housing 45D, 45E As shown in FIGS. 9 and 10, IMD header 48D, 48E defines an inner chamber 49D, 49E, respectively. In some examples, IMD header 48D, 48E may define an inner chamber that includes at least three substantially perpendicular inner surfaces. According to the examples of FIGS. 9 and 10, antenna 50D, 50E may be formed such that an exterior surface of antenna 50 comprising first portion 52, second portion 54, and third portion 56 are of a substantially similar shape as inner surfaces of an interior chamber of IMD header 50D, 50E. In some examples, as depicted in FIG. 10, antenna 50 may be formed of substantially smaller size than an interior chamber of IMD header 48. As shown in the example of FIG. 10, antenna 50E may be coupled to components of IMD 22E (e.g., electrical circuitry housed within IMD housing 45E) via one or more conductive members 99.

In other examples, as depicted in FIG. 9, first, second, and third portions 52, 54, and 56 of antenna 50 may be sized and shaped such that they are substantially conformal to inner surfaces (e.g., interior walls) of an interior chamber of IMD header 48. For example, as shown in FIG. 9, the first, second, and third portions 52, 54, 56 of antenna 50D are each respectively sized and shaped to conform to first, second, and third inner surfaces of header portion 48D.

Although not depicted in FIGS. 9 and 10, the first, second, and third portions 52, 54, and 56 of antennas 50D, 50E may be formed around a molding material. The molding material may be, for example, a polymer material (e.g., a plastic), or a ceramic material. It may be desirable for the molding material to be a non-conductive material that does not interfere with electrical properties of antennas 50D, 50E. In some examples, also not depicted in FIGS. 9 and 10, an exterior of antennas 50D, 50E may be surrounded by a molding material. According to these examples, a molding material formed around an exterior of antennas 50D, 50E may be the same as a material around which antennas 50D, 50E are formed. In other examples, a molding material formed around an exterior of antennas 50D, 50E may be a different material than a molding material that antennas 50D, 50E are formed around.

Figure 11:
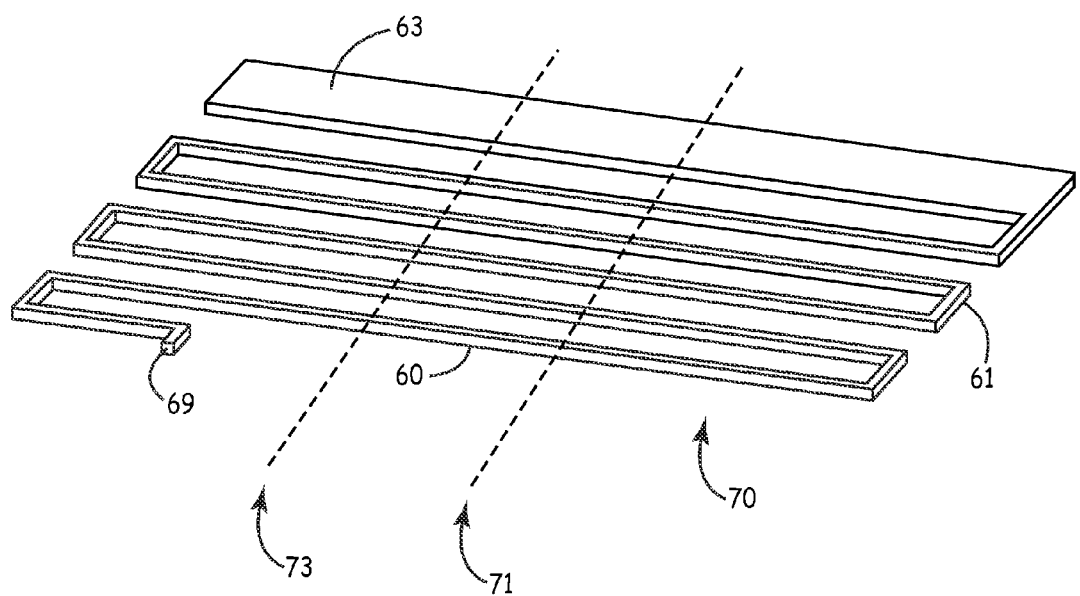
FIGS. 11 and 12 are conceptual diagrams that illustrate formation of a 3D antenna consistent with this disclosure.
Figure 12:
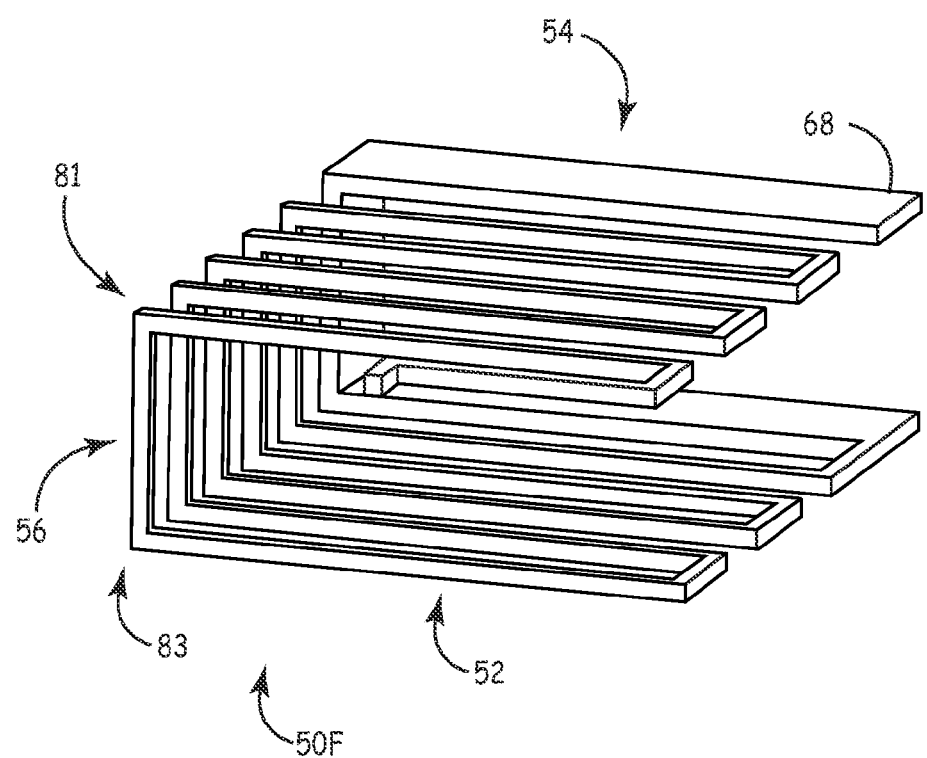

FIGS. 11 and 12 illustrate generally one example of a manufacturing process that may be used to form a three-dimensional antenna 50 as described herein. To form antenna 50, a substrate (not shown) may be provided. The substrate may be formed of a conductive material, such as a metal. Specific non-limiting examples of conductive materials that may be used as a substrate include aluminum, niobium, titanium, gold, and platinum, or their alloys. In some examples, the substrate may comprise a thin sheet of metallic material or a dielectric material. In some examples, the substrate may comprise a thin sheet of metallic material (or other conductive material) formed on a surface of a dielectric substrate. According to these examples, a thin film of metallic material may be formed by various techniques known in the art, for example chemical vapor deposition, sputtering, electro-plating, electro-less plating, and like techniques.

As shown in FIG. 11, the substrate may be used to form a one-dimensional (1D) serpentine (or meandering) structure 70 arranged in a single plane. The 1D serpentine structure 70 may include a plurality of substantially parallel horizontally arranged segments 60 coupled to one another on alternating ends by a plurality of substantially parallel vertically arranged segments 61. The plurality of substantially parallel horizontally arranged segments 60 may be arranged in the single plane. As also shown in FIG. 11, the 1D serpentine structure 70 may further include coupling structure 69 and a one-dimensional (1D) antenna loading structure 63.

The 1D serpentine structure 70 depicted in FIG. 11 may be formed from a substrate by a variety of mechanisms known in the art. For example, substrate 70 may be cut to form structure 70. In another example, the substrate may be stamped to form structure 70. Other mechanisms to form 1D serpentine structure 70 are also contemplated and consistent with this disclosure. For example, the 1D serpentine structure 70 may be formed by chemical vapor deposition, physical vapor deposition, (e.g., sputtering, pulsed laser deposition, or the like), electro-plating, electroless plating, or any other coating and/or metallization process.

Figure 8:
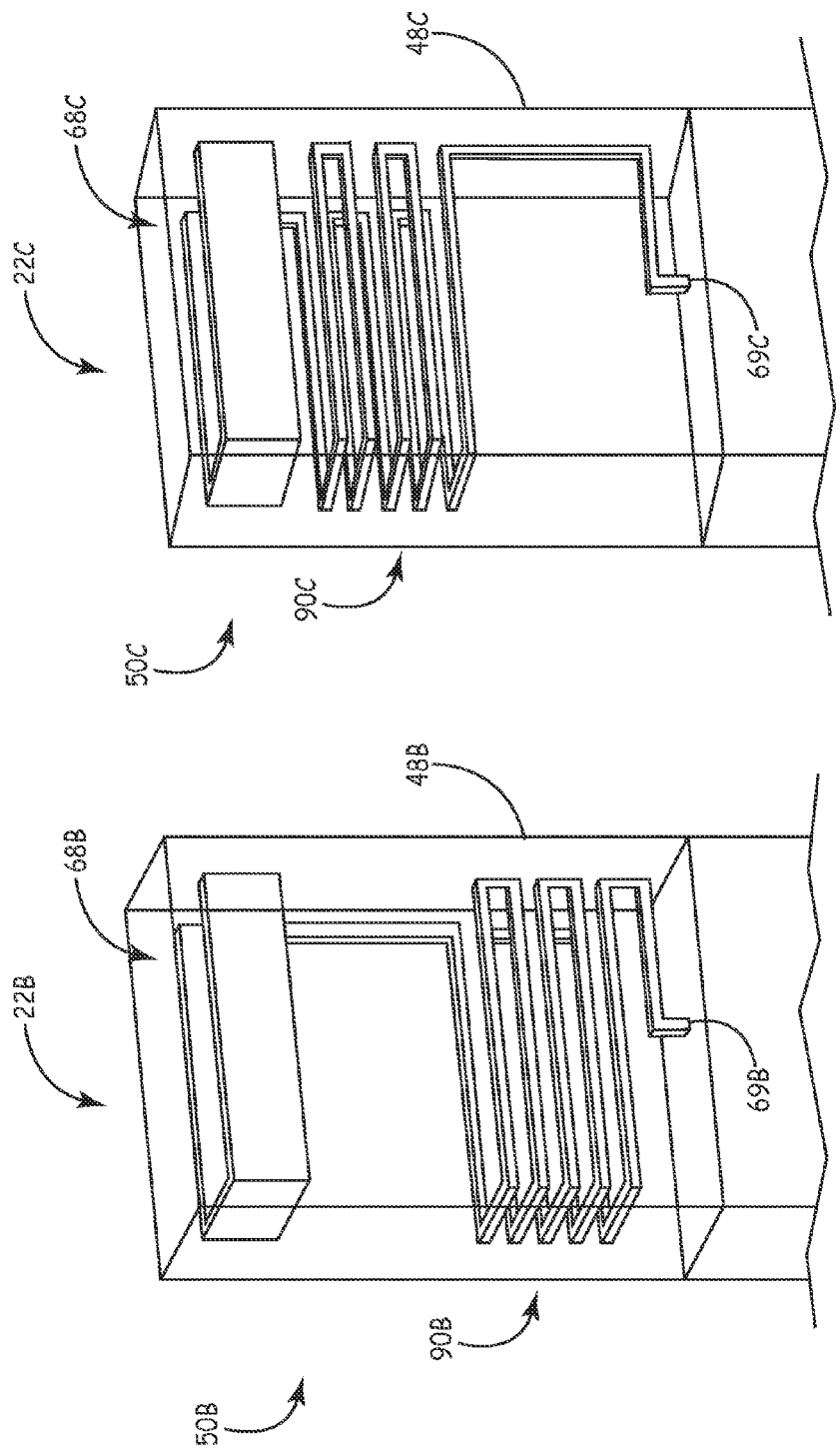
FIGS. 8A-8B are conceptual diagrams illustrating alternative examples of a 3D antenna disposed within an IMD consistent with this disclosure.

The 1D serpentine structure 70 depicted in FIG. 11 may be bent, or otherwise formed, to create three-dimensional antenna 50F depicted in FIG. 12. For example, 1D serpentine structure may be bent at two positions (e.g., along lines 71 and 73 in the example of FIG. 11) along a length of horizontally arranged segments 60 (arranged in the third plane as described above with respect to FIGS. 3-6) to form the first portion 52 and second portion 54 of a 3D antenna 50F. As shown in FIG. 12, bending of 1D serpentine structure 70 at positions 71 and 73 creates corresponding junctions 81, 83 between third portion 56 and first and second portions 52, 54, respectively. In some examples, the 1D serpentine structure 70 may be bent at positions selected based on desired characteristics of antenna. For example, structure 70 may be bent at positions selected to create a desired external form factor of antenna 50F (e.g., to conform to a housing (e.g., header portion 48 as depicted in FIG. 8). In other examples, structure 70 may be bent at positions to achieve a desired performance of antenna 50F (e.g., a gain ratio of antenna 50F).

Figure 13:
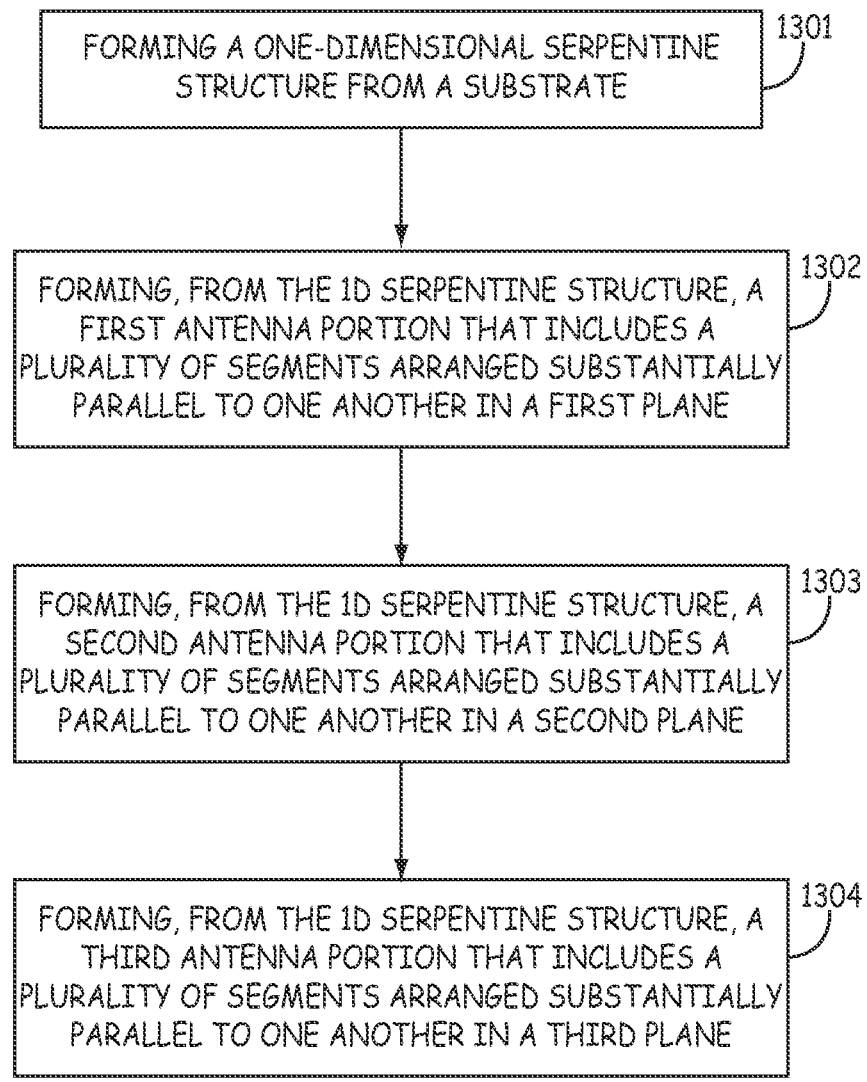
FIG. 13 is a flow chart diagram that illustrates one example of a method of forming a 3D antenna consistent with this disclosure.

FIG. 13 illustrates generally one example of a method of forming a three-dimensional serpentine antenna consistent with the techniques of this disclosure. The method includes forming a 1D serpentine structure 70 from a substrate (1301). The 1D serpentine structure may includes a plurality of segments 60 horizontally arranged in a plane. The plurality of segments of the 1D serpentine structure 70 may be coupled to one another on alternating ends by a plurality of substantially parallel vertically arranged segments 61. In one example, the 1D serpentine structure 70 is formed by cutting the substrate. In another example, the 1D serpentine structure 70 is formed by stamping the substrate.

The method further includes forming, from the 1D serpentine structure 70, a first antenna portion 52 that includes a plurality of segments arranged substantially parallel to one another in a first plane (1302). The first antenna portion 52 may be formed by bending the 1D serpentine structure 70 at a first position 71. The method further includes forming a second antenna portion 54 that includes a plurality of segments arranged substantially parallel to one another in a second plane (1303). The second portion may be substantially parallel to the first portion. The second antenna portion 54 may be formed by bending the 1D serpentine structure 70 at a second position 73. The method further includes forming a third antenna portion 56 that includes a plurality of segments arranged substantially parallel to one another in a third plane arranged substantially perpendicular to the first plane and the second plane (1304). The third antenna portion may be formed by forming the first and second antenna portions. The plurality of segments of the third portion are coupled between segments of the first and second portions. In one example, forming the antenna includes bending the 1D serpentine at least two positions along the plurality of segments horizontally arranged in a plane. In one example, the third plane of the antenna is the plane in which the 1D serpentine structure 70 was arranged.

Figure 14:
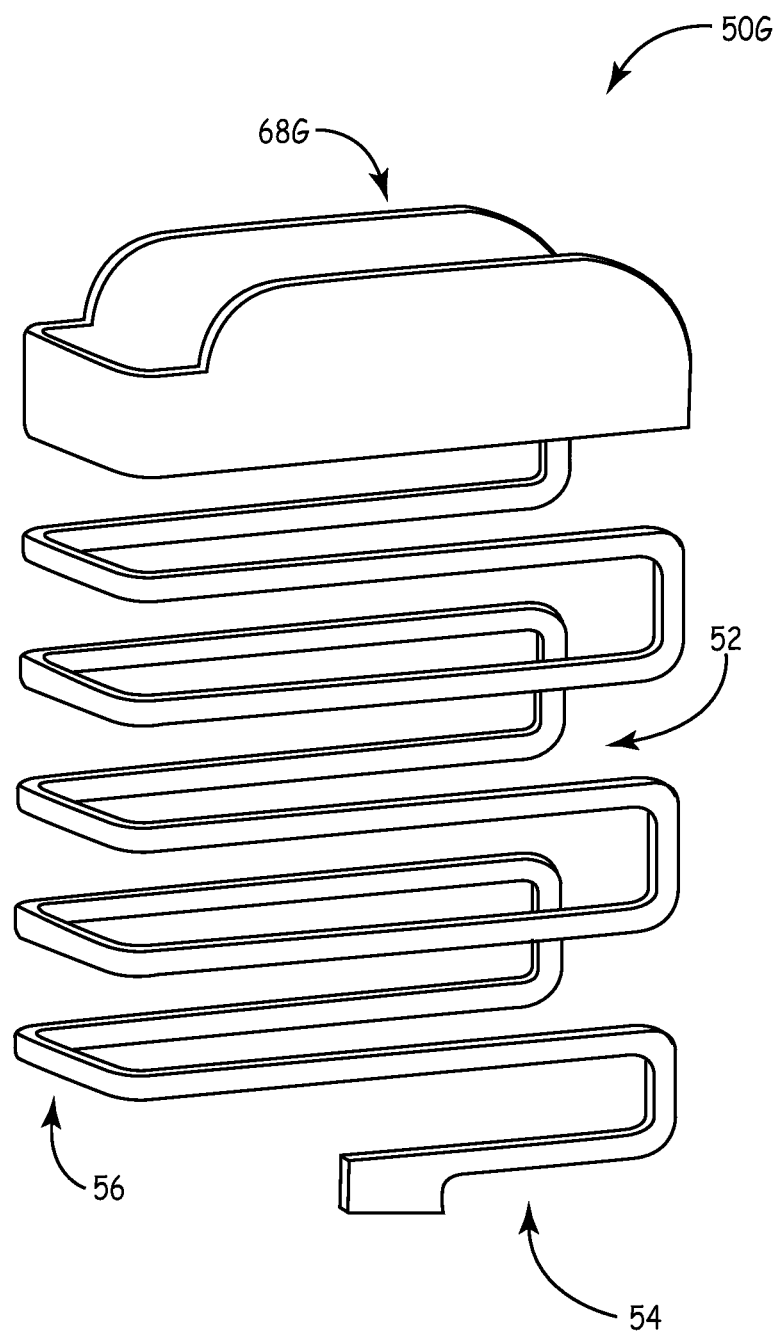
FIG. 14 is a conceptual diagram illustrating one example of a 3D antenna consistent with this disclosure.

FIG. 14 illustrates one alternative example of a 3D antenna 50G consistent with this disclosure. The antenna 50G of FIG. 11 is similar to the antenna 50 depicted in FIGS. 3-6. However, antenna 50 of FIGS. 3-6 shows coupling between the plurality of segments of antenna 50 as substantially rectangular, or forming an edge at a junction between segments. In contrast, FIG. 14 depicts one example of a 3D antenna 50G that includes rounded junctions 51G between the plurality of segments.

Antenna 50G also differs from antenna 50 in that antenna loading portion 68G includes substantially arcuate edges 57G. The arcuate edges 57G of antenna loading portion 68G may be formed to conform to a corresponding mating portion of an upper interior surface of a housing or chamber in which antenna 50G is to be disposed, for example a header portion 48D of an IMD housing 45D as depicted in FIG. 9.

A three-dimensional antenna 50 as described herein may be advantageous for a number of reasons. For example, antenna 50 may provide desirable gain characteristics while having a relatively small volumetric footprint. For example, antenna 50 may be formed to a height of less than 5 millimeters, and a volumetric footprint less than 0.1 cubic centimeters. In some examples, an antenna 50 as described herein may have similar gain characteristics (e.g., gain ratio) to other known antenna designs that have a much greater height and/or a much larger volumetric footprint.

Antenna loading structure 68 may also provide various performance benefits. For example, loading structure 68 may provide for improved capacitive loading, which may provide for an improved impedance match for antenna. For example, loading structure 68 may provide for improved impedance matching between antenna 50 and a housing 45 of an IMD, which serves as an electrical ground reference for electrical circuitry 43 of an IMD 22 (e.g., as shown in FIG. 2). Loading structure 68 may further enable an impedance of antenna 50 to be less sensitive to distance between an inner surface of a header portion (e.g., header portion 48 illustrated in FIG. 2). As such, an impedance of antenna 50 may be less sensitive to manufacturing process inconsistencies.

Antenna 50 may also be desirable due to an external profile of antenna 50 formed by the first, second, and third portions 52, 54, and 56. For example, it may be desirable to dispose antenna 50 within a housing or header of an implantable medical device (e.g., housing 45, header 48 of IMD 22 depicted in FIG. 2) or another device. In some examples, a housing, or a header of a device may define an interior space that is substantially rectangular shaped. The housing or header may include a plurality of perpendicularly arranged inner surfaces, and the first, second, and third portions 52, 54, and 56 may each be configured to conform to each of the inner surfaces of the housing or header. Accordingly, antenna 50 may be arranged to consume a minimum amount of space within an IMD housing 45, or header of an IMD housing 45, as depicted in FIG. 2 for example.

In some examples, one or more inner surfaces of a header 48 or housing of an IMD (e.g., IMD 22 depicted in FIG. 2) may not be substantially flat. According to these examples, segments of an antenna 50 as described herein may be substantially curved to conform to one or more curved inner surfaces (e.g., walls) of a chamber in which the antenna 50 is disposed (e.g., an inner chamber of an IMD housing 45). In some examples, some segments may be curved, while other segments may be substantially straight. For example, where a first inner surface of a chamber is substantially curved, and a second inner surface of the chamber is substantially flat, a first portion (e.g., first portion 52) of an antenna 50 may include substantially curved segments to conform to the first inner surface, while a second portion of the antenna (e.g., second portion 54 or third portion 56) may include substantially straight segments to conform to the second inner surface.

Additionally, because antenna 50 defines an interior space between the first, second and third portions 52, 54, and 56, the interior space of antenna 50 may be utilized to arrange other components of antenna 50. For example, one or more of electrically circuitry 43, battery, power source 47, or any other component of IMD 22 may be disposed within an interior space defined by antenna 50.

Antenna 50 as described herein may further be easy to manufacture and/or to conform to a desired form factor such that antenna 50 may be disposed within a variety of IMDs of various sizes and shapes. Further, as described above, antenna 50 may be easily formed with different ratios between a length of segments of third portion 56 with respect to a length of segments of first and second portions 52 and 54. Accordingly, antenna 50 may be "tuned," or configured to a specific implementation, by merely changing a position at which the horizontal segments of 1D serpentine structure 70 (as depicted in FIG. 11) are bent. In one example, antenna 50 may be "tuned" to a particular communication frequency for the transmission and/or reception of signals. In one example, antenna 50 may be tuned to a communication frequency of around 400 mHz. Other frequencies are also contemplated and consistent with the techniques of this disclosure.

Various embodiments of the invention have been described. These and other embodiments are within the scope of the following claims.

The invention claimed is:

1. A device comprising:
a telemetry module; and
an antenna coupled to the telemetry module, the antenna comprising:
a first antenna portion comprising a plurality of segments arranged substantially parallel to one another in a first plane;
a second antenna portion comprising a plurality of segments arranged substantially parallel to one another in a second plane; and
a third antenna portion comprising a plurality of segments arranged substantially parallel to one another in a third plane, wherein the plurality of segments of the third antenna portion are coupled between segments of the first and second antenna portions, and wherein the third plane is arranged substantially perpendicular to the first plane and the second plane,
wherein at least one of the first and second antenna portions comprises an antenna loading structure and a coupling structure configured to electrically connect the antenna to the telemetry module, wherein the antenna loading structure has at least one dimension substantially greater than a corresponding dimension of the plurality of segments of the first and second antenna portions, and wherein the antenna loading structure is arranged toward an end of the antenna not electrically connected to the telemetry module and the coupling structure is arranged toward an end of the antenna opposite the antenna loading structure.

2. The device of claim 1, wherein the antenna is disposed within a header portion of an implantable medical device (IMD).

3. The device of claim 2, wherein the header portion of the device includes at least first, second, and third inner surfaces, wherein the first inner surface is arranged substantially perpendicular to the second inner surface, and wherein the third inner surface is arranged substantially perpendicular to the second inner surface; and
wherein the antenna is disposed within the header portion such that the first antenna portion is arranged substantially parallel to the first inner surface, the second antenna portion is arranged substantially parallel to the third inner surface, and wherein the third antenna portion is arranged substantially parallel to the second inner surface.

4. The device of claim 3, wherein the first, second and third antenna portions are each arranged substantially conformal to at least one of the first, second, and third inner surfaces of the header portion.

5. The device of claim 3, wherein an outer surface area of the first, second, and third antenna portions each comprises a substantially similar shape to at least one of the first, second, and third inner surfaces of the header portion of the IMD.

6. The device of claim 1, wherein the antenna comprises a first segment;
a second segment integral to the first segment and arranged substantially perpendicular to the first segment;
a third segment integral to the second segment and arranged substantially perpendicular to the first and second segment;
a fourth segment integral to the third segment and arranged substantially perpendicular to the third segment and substantially parallel to the second segment; and a fifth segment integral to the fourth segment and arranged substantially perpendicular to the fourth segment and parallel to the first segment, wherein the first antenna portion comprises the second, third, and fourth segments; and wherein the third antenna portion comprises the first and fifth segments.

7. The device of claim 6, wherein the first, second, third, fourth, and fifth segments form a first meandering section of the antenna, and further comprising:

at least one second meandering section of the antenna.

8. The device of claim 6, further comprising:

a sixth segment integral to the fifth segment and arranged substantially perpendicular to the fifth segment and substantially parallel to the fourth segment, wherein the second antenna portion comprises the sixth segment.

9. The device of claim 1, wherein the plurality of segments of the first and second antenna portions are substantially straight.

10. The device of claim 1, wherein the plurality of segments of the first and second antenna portions include at least on arcuate section.

11. The device of claim 1, wherein the plurality of segments of the first and second antenna portions have a length substantially greater than a corresponding length of the plurality of segments of the third antenna portion.

12. The device of claim 11, wherein the plurality of segments of the first antenna portion and the second antenna portion have a length 2-3 times greater than the corresponding length of the plurality of segments of the third antenna portion.

13. The device of claim 1, wherein the device comprises an implantable medical device.

14. The device of claim 1, wherein the device comprises a communication module.

15. The device of claim 1, wherein the antenna sequentially:

traverses, via a first one of the plurality of segments of the first antenna portion, the first plane in a first direction;

traverses, via a first one of the plurality of segments of the third antenna portion, the third plane substantially perpendicular to the first plane in a second direction;

traverses, via a first one of the plurality of segments of the second antenna portion, the second plane substantially perpendicular to the third plane and parallel to the first plane in a third direction substantially opposite the first direction;

traverses the second plane in a fourth direction substantially perpendicular to the first, second, and third directions;

traverses, via a second one of the plurality of segments of the second antenna portion, the second plane in the first direction;

traverses, via a second one of the plurality of segments of the third antenna portion, the third plane in a fifth direction substantially opposite the second direction;

traverses, via a second one of the plurality of segments of the first antenna portion, the first plane in the third direction; and traverses the first plane in the fourth direction substantially perpendicular to the first, second, and third directions.

16. The device of claim 1, wherein the antenna loading structure is formed of one of the first antenna portions, one of the second antenna portions, and one of the third antenna portions.

17. An antenna comprising:

a first antenna portion comprising a plurality of segments arranged substantially parallel to one another in a first plane;

a second antenna portion comprising a plurality of segments arranged substantially parallel to one another in a second plane; and a third antenna portion comprising a plurality of segments arranged substantially parallel to one another in a third plane, wherein the plurality of segments of the third antenna portion are coupled between segments of the first and second antenna portions, and wherein the third plane is arranged substantially perpendicular to the first plane and the second plane, wherein at least one of the first and second antenna portions comprises an antenna loading structure and a coupling structure configured to electrically connect the antenna to one or more electrical components, wherein the antenna loading structure has at least one dimension substantially greater than a corresponding dimension of the plurality of segments of the first and second antenna portions, and wherein the antenna loading structure is arranged toward an end of the antenna not electrically connected to the one or more electrical components and the coupling structure is arranged toward an end of the antenna opposite the antenna loading structure.

18. The antenna of claim 17, wherein the antenna comprises a first segment;

a second segment integral to the first segment and arranged substantially perpendicular to the first segment;

a third segment integral to the second segment and arranged substantially perpendicular to the first and second segment;

a fourth segment integral to the third segment and arranged substantially perpendicular to the third segment and substantially parallel to the second segment; and a fifth segment integral to the fourth segment and arranged substantially perpendicular to the fourth segment and parallel to the first segment, wherein the first antenna portion comprises the second, third, and fourth segments; and wherein the third antenna portion comprises the first and fifth segments.

19. The antenna of claim 18, further comprising:

a sixth segment integral to the fifth segment and arranged substantially perpendicular to the fifth segment and substantially parallel to the fourth segment, wherein the second antenna portion comprises the sixth segment.

20. A method of forming a three-dimensional antenna, comprising:

forming, from a substrate, a one-dimensional serpentine structure that comprises a plurality of segments arranged substantially parallel to one another in a plane; and forming, from the one-dimensional serpentine structure, a three-dimensional antenna that includes a first portion that includes a plurality of segments arranged substantially parallel to one another in a first plane, a second portion that includes a plurality of segments arranged substantially parallel to one another in a second plane, and a third portion that includes a plurality of segments arranged substantially parallel to one another in a third plane, wherein the plurality of segments of the third portion are coupled between segments of the first and second portions, and wherein the third plane is arranged substantially perpendicular to the first plane and the second plane, wherein at least one of the first and second antenna portions comprises an antenna loading structure and a coupling structure configured to electrically connect the antenna to one or more electrical components, wherein the antenna loading structure has at least one dimension substantially greater than a corresponding dimension of the plurality of segments of the first and second antenna portions, and wherein the antenna loading structure is arranged toward an end of the antenna not electrically connected to the one or more electrical components and the coupling structure is arranged toward an end of the antenna opposite the antenna loading structure.

21. The method of claim 20, wherein the third plane corresponds to the plane in which the plurality of segments of the one-dimensional serpentine structure are arranged.

22. The method of claim 20, wherein forming, from the 1D serpentine structure, a three-dimensional antenna comprises:
bending the 1D serpentine structure at at least two positions along the plurality of segments horizontally arranged in a plane.

23. The method of claim 22, further comprising:
bending the 1D serpentine at the at least two position selected based on a desired performance characteristic of the three-dimensional antenna.

24. The method of claim 22, further comprising bending the 1D serpentine at the at least two positions selected based on a shape of the three-dimensional antenna.

25. The method of claim 20, further comprising:
coupling the three-dimensional antenna to telemetry circuitry of an implantable medical device (IMD) to facilitate communications of the IMD, wherein the one or more electrical components comprise the telemetry circuitry.

* * * * *